US008111076B1

(12) United States Patent
Gensler

(10) Patent No.: US 8,111,076 B1
(45) Date of Patent: Feb. 7, 2012

(54) METHOD AND APPARATUS FOR DETERMINATION OF PLANT CANOPY REHYDRATION RATE AND MAGNITUDE OF PLANT CANOPY WATER STORAGE

(76) Inventor: William G. Gensler, Tucson, AZ (US)

( * ) Notice: Subject to any disclaimer, the term of this patent is extended or adjusted under 35 U.S.C. 154(b) by 0 days.

(21) Appl. No.: 12/657,353

(22) Filed: Jan. 19, 2010

(51) Int. Cl.
*G01R 27/26* (2006.01)
(52) U.S. Cl. .......... 324/679; 324/72; 324/664; 324/658; 47/49; 73/73; 73/304 C; 73/304 R; 239/71
(58) Field of Classification Search .................... 324/679
See application file for complete search history.

(56) References Cited

U.S. PATENT DOCUMENTS

| | | | |
|---|---|---|---|
| 3,967,198 A * | 6/1976 | Gensler ........................... 324/72 |
| 6,870,376 B1 * | 3/2005 | Gensler ........................ 324/664 |
| 7,069,692 B2 * | 7/2006 | Kuiper et al. ................. 47/62 A |
| 7,229,546 B1 * | 6/2007 | Gensler .......................... 205/792 |
| 7,648,836 B1 * | 1/2010 | Scott ............................... 436/39 |

* cited by examiner

Primary Examiner — Melissa Koval
Assistant Examiner — Benjamin M Baldridge

(57) ABSTRACT

This invention is concerned with a method for measuring the canopy rehydration pulse during the period of water application. During the rehydration process water leaks from the trunk xylem tubes into the sapwood extraxyllary region. A water content sensor in this region monitors the magnitude and timing of this leakage water thereby giving a measure of the magnitude and timing of the upward flow of water. The rehydration pulse is quantified by a sequence of measurements of sapwood water content: an initial measurement of water content just prior to water application, then measurement of water content during water application. The difference between the values obtained in the two measurements yields a measure of the leakage water in the extraxyllary region and, in turn, the magnitude and timing of the rehydration pulse. Determination of the onset and termination of the rehydration pulse is used to optimize the duration of water application.

1 Claim, 4 Drawing Sheets

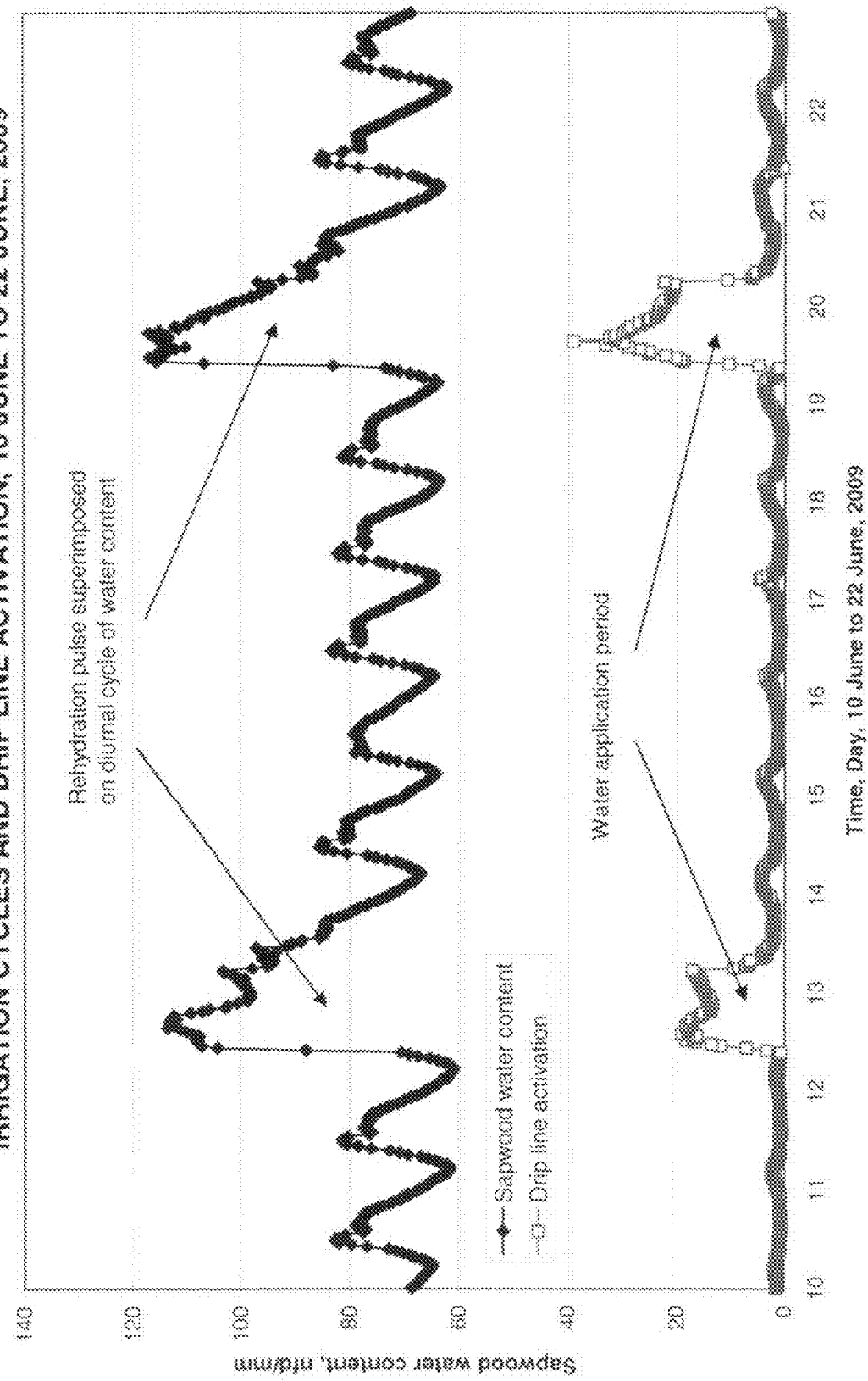

Figure 1:
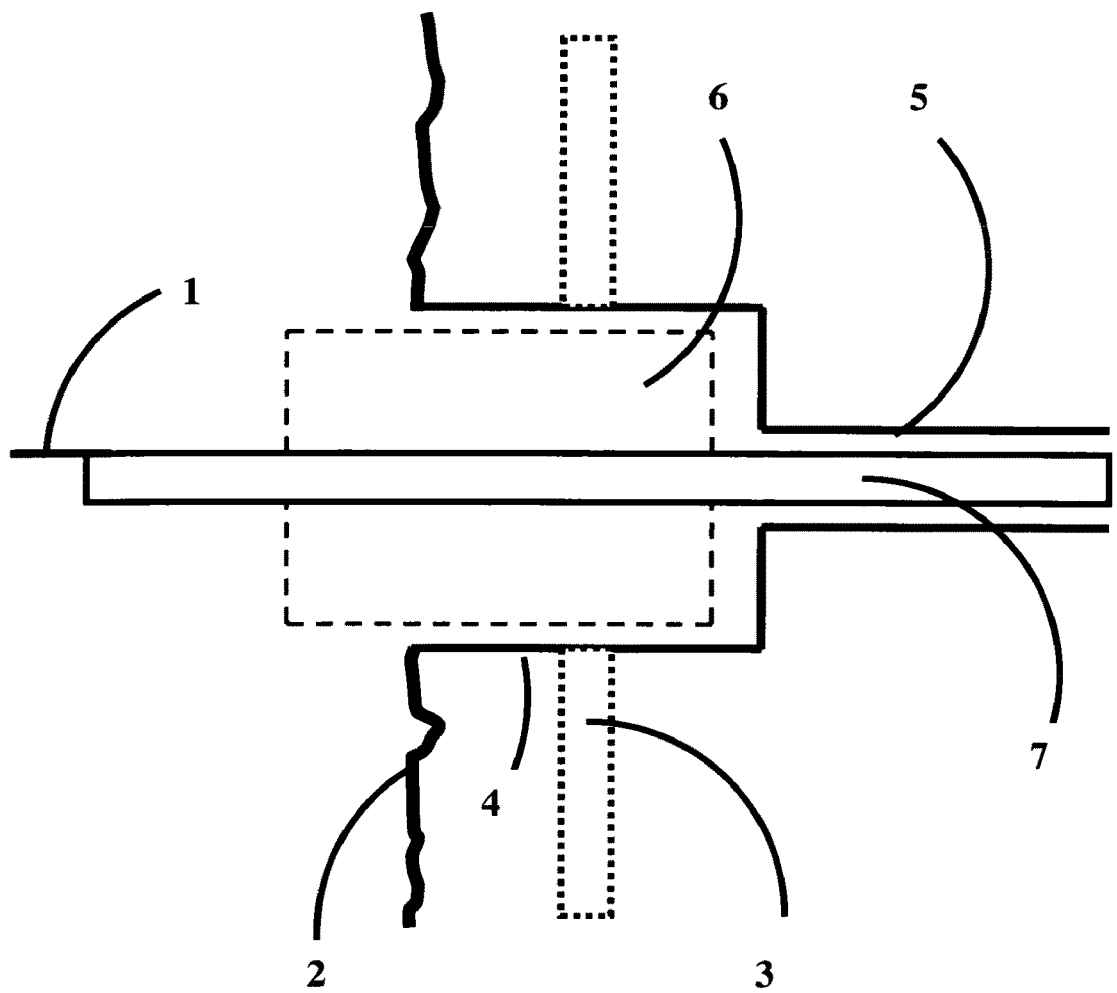

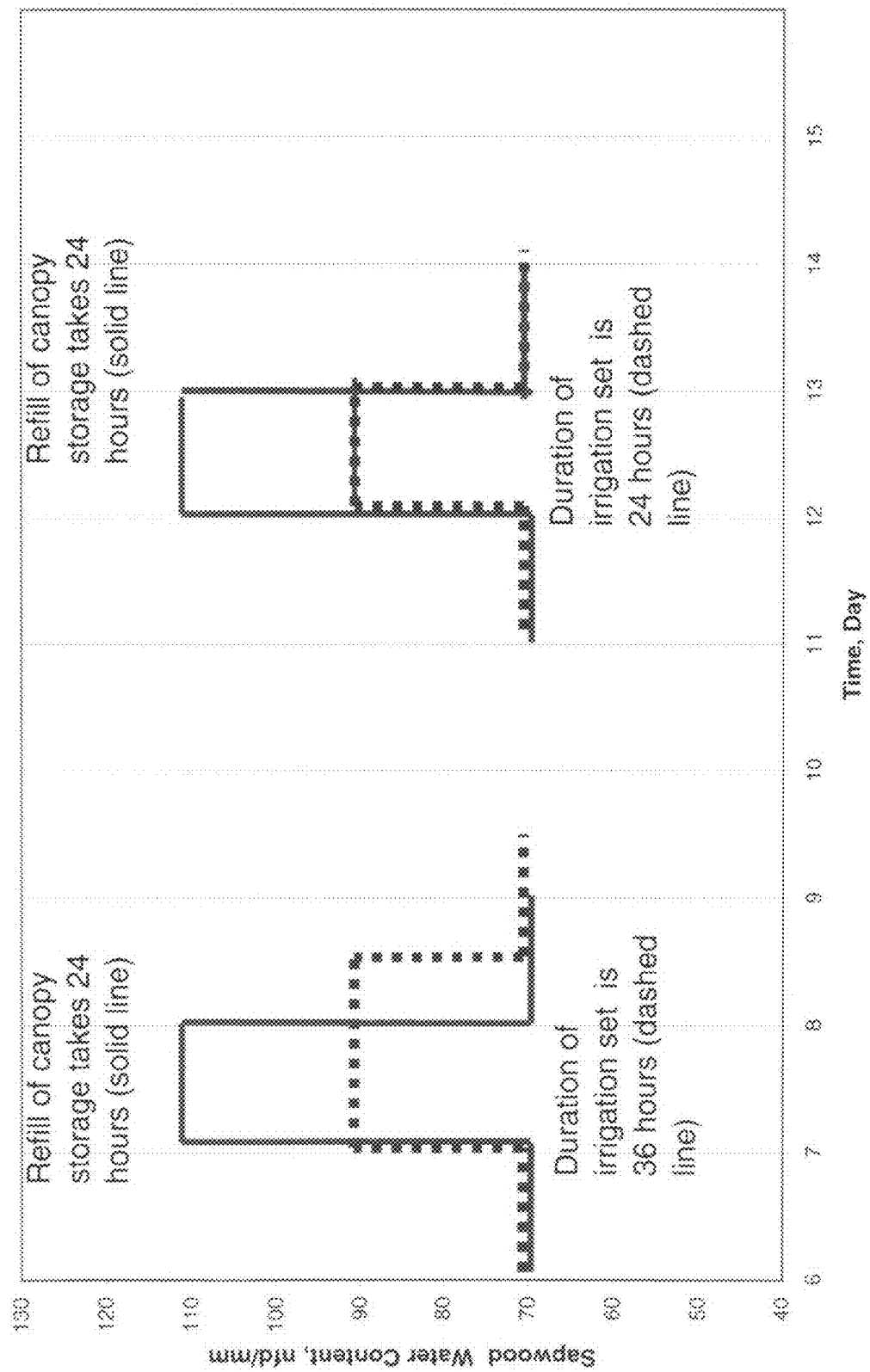
FIG 4 ADJUSTMENT OF DURATION OF IRRIGATION SET TIME TO MATCH CANOPY STORAGE REFILL TIME

METHOD AND APPARATUS FOR DETERMINATION OF PLANT CANOPY REHYDRATION RATE AND MAGNITUDE OF PLANT CANOPY WATER STORAGE

REFERENCES CITED

U.S. Pat. No. 6,870,376 B1 2005 Method and Apparatus for Determining Plant Water Content Gensler, W. G.
Evert, R. (2006) Esau's Plant Anatomy. 3rd Ed. Wiley, Hoboken, N.J.
Reyes, J. F., J. Jara and R. Jeldres (2007) Design Parameters Evaluation of a SapFlow Meter for Small Trees. IDESIA (Chile) Volume 25, #1, 53-62, January-April, 2007
Gensler, W. (1999) Measuring and interpreting diurnal activity in the main stem of trees. In Tree Ring Analysis, Biological, Methodoligical and Environmental Aspects. R Wimmer and R, E. Wetter, eds. CABI Publishing Wallingford, OX, UK.
Taiz, L. and E. Zeiger (2006) Plant Physiology Sinauer Associates, Inc. Publishers, Sunderland, Mass.
Salisbury, F. B. and C. W. Ross (1992) Plant Physiology, 4th Ed. Wadsworth Publishing Company, Belmont, Calif.
Sperry, J. S. and M. T. Tyree (1988) Mechanism of water stress-induced xylem embolism. Plant Physiology 88:581-587.
Zimmermann, M. H. (1983) Xylem structure and ascent of sap Springer-Verlag, Berlin.

FIELD OF THE INVENTION

This invention generally relates to botanical and agricultural measurements and more particularly a method and apparatus that utilizes a mechanical measurement and an electrochemical measurement

DEFINITIONS

The term "sapflow" is defined herein as the flow of water in the xylem tubes of the main stem of the plant.
The term "canopy" is defined herein as the total water storage locations in the trunk, branches, stems, leaves and fruit of a plant

PRIOR ART I

Sapflow has been extensively measured using a heat pulse method (Reyes, et al, 2007). The apparatus consists of a source of thermal energy placed at one point in the stem or trunk of the plant and a thermal monitoring device such as a thermocouple at a second nearby point in the stem or trunk. A pulse of heat energy is applied at the first point. This heat energy passes into the xylem stream of the plant and is carried along the xylem tubes to the region of the second point wherein the temperature of the fluid stream rises. The timing between the application of the heat pulse at the first point and the increase in measured temperature at the second point gives an indication of the speed of fluid movement in the xylem tube. The power level of the heat pulse in in the order of tenths of a watt and the distances between the two points in the order of tens of millimeters. To convert the rate of fluid movement to a volume of fluid movement estimates must be made as to the size and quantity of the xylem tubes. This estimate can be made more precise by the use of multiple sources of heat energy and measuring devices.

PRIOR ART II

Gensler (U.S. Pat. No. 6,870,376 B1, 2005, Gensler W., 1999)) teaches a method and apparatus to measure plant water content. The method and apparatus in this Patent is an electrode implanted in the extracellular region of plant tissue. Water in the extracellular region adsorbs on the surface of the electrode. The amount of wetted surface area is proportional to the water content in the tissue as a whole. Changes in the wetted surface area yield changes in the water content of the tissue. The apparatus functions as a "water dipstick" in the same manner as an "oil dipstick" in an automobile. Within the scope of U.S. Pat. No. 6,870,376 B1, the sensing electrode can be located in the sapwood to yield a measure of the diurnal cycle of water content. The phase and amplitude of the measured diurnal cycle of sapwood water content remains essentially the same over multi day period which occur between water applications in irrigated agricultural fields. The minimum value of the diurnal water content cycle elicits a decline due to the loss of water from the plant canopy into the atmosphere. This decline in water content in the sapwood gives a measure of water loss during the time interval between water applications.

This invention utilizes the same apparatus as in U.S. Pat. No. 6,870,376 B1. The method is different from the method in U.S. Pat. No. 6,870,376 B1. This difference will now be explained The measured water content, MWC, in the extraxyllary region is the sum of two components: 1) water content, $WC_D$, that has its origin in the normal course of diurnal activity associated with the living cells in the sapwood, 2) water content, $WC_L$, that has its origin from leakage of the xylem tubes during periods of high negative pressure in the xylem tubes during rehydration of the plant. Mathematically, $$MWC(t)=WC_D(t)+WC_L(t) \tag{1}$$

These variables are expressed as functions of time. The diurnal water content, $WC_D(t)$, is always present. This is the water content that is addressed in the method and apparatus of U.S. Pat. No. 6,870,376 B1. The leakage water content, $WC_L(t)$, is present only during periods of high negative pressure in the xylem tubes. It is pulse-like water content superimposed on the normal cyclic diurnal water content. This high negative pressure occurs when the plant tries to pull water up from the soil in an attempt to rehydrate the upper part of the plant during water application to the soil. This is the water content that is addressed in this invention.

Further discussion will be made in the Objects and Advantages Section below.

OBJECTS AND ADVANTAGES

Object of the Invention

The object of this invention is to measure the total water increase in the plant canopy during the period of time wherein water is applied to the soil.

The standard agricultural irrigation cycle has two time intervals: the interval between water application and the interval during water application. This invention is concerned with the interval during water application.

Two sequential decisions are required to set the timing and magnitude of the irrigation cycle: when to water and how much to water. The decision concerning when to water is based on the minimum value of the daily diurnal water content cycle. When the minimum value reaches a lower bound for optimum water use efficiency, water is applied. The next question is how much water to apply. For optimum water use efficiency, the decision concerning how much water to apply is based on the premise that one should apply just enough water to the soil storage volume to completely fill the plant storage volume. Any further application of water to the soil volume will result in banking the water in the soil volume wherein it could be partially lost due to downward percolation.

During the period between water applications, the plant water storage volume is depleted along with the soil water storage volume. This occurs in spite of the process of transferring water from soil to plant that occurs each day. When the two storage volumes, soil and plant, are depleted a decision is made to apply water. Water application results in a recharge of the soil storage volume and plant storage volume (plant canopy). This invention concerns a method and apparatus to measure the magnitude and timing of the recharge (rehydration) of the plant storage volume (plant canopy).

Recharge of the above ground plant water storage volume is accomplished by passing water through a set of tubes in the trunk. These tubes are referred to as the xylem (Evert, 2006). The characteristic of the xylem which is utilized in this invention will now be discussed.

Principle of Operation

This invention is based on the presence of "designed leaks" in the xylem tubes of the main stem of plants (Zimmermann, page 44, 1983; Sperry and Tyree, 1988). Movement of water upward from the roots to the upper part of the plant is caused by a negative pressure gradient in the xylem tubes. Xylem tubes are sealed tubes that carry water upward from the roots to the upper part of the plant (Taiz and Zeiger, 2006). The greater the negative pressure, the stronger the volume of fluid transfer. Structurally as the negative pressure increases, the pressure difference between the inside of the tube and the outside of the tube increases. At some point in time, this pressure differential becomes unsustainable and individual xylem tubes fracture at pores in the walls of the sealed tube and fluid leaks out into the extraxyllary open space outside the tube. Zimmermann termed these "designed leaks" (Zimmermann, 1983, page 44). The operating principle of this invention is the monitoring of the magnitude and timing of this leakage.

This leakage is an increase in water content in the extraxyllary region over and above the normal water content in the extraxyllary region. Equation 1 above describes the situation in algebraic form. This water arises from a specific physiological event, namely, a leak in the normally sealed xylem tube. Magnitude and timing of the water from these leaks is proportional to the magnitude and timing of the pressure differential between the inside and outside of the xylem tubes. The pressure outside the xylem tube is ambient pressure (Salisbury and Ross, 1992). The pressure inside the tube becomes more negative in concert with an increase in upward flow of water in the tube. The magnitude and timing of the leakage water becomes a measure of the magnitude and timing of water movement upward within the xylem tube.

Since the leakage arises from multiple xylem tubes, the magnitude and timing of the leakage gives an approximate measure of the volume of water movement upward in the entire array of xylem tubes.

A sensor electrode resident in the extraxyllary region of the sapwood is used to monitor the magnitude and timing of this leakage water.

Implanting the Sensor Electrode in the Sapwood

The trunk of a tree consists of several tissue concentric layers or rings. The outermost layer is bark tissue containing phloem conducting tissue. Then there is a thin layer of reproductive tissue termed the cambium. This is followed by a layer of sapwood and finally a layer of heartwood at the center of the trunk. The sapwood is the tissue layer that contains the xylem tubes. FIG. 1 shows the sensor electrode resident within the sapwood layer.

In order to assure that the total active sensor electrode surface area in homogeneous sapwood is a known value, a special procedure must be employed. A large diameter hole must be drilled into the trunk such that the bottom of this hole is located at a radius less than the radius of the cambium. An electrical non conducting implant such as a nylon set screw is then threaded into this hole. A hole is then drilled into and through the implant. The drill bit then continues into the sapwood for a known distance past the end of the implant. The drill bit is removed leaving the successive holes shown in FIG. 1. The sensor electrode is passed though the hole in the implant and continues into the hole in the sapwood until it reaches the bottom of the hole in the sapwood. The result of this procedure is a known active area of sensor electrode surface within homogeneous sapwood.

Method of Making a Measurement of Interfacial Capacitance Changes

The sensor electrode itself is the long filament of metal shown in FIG. 1. Part of the surface area of the sensor electrode is wetted by the adsorbed water from the xylem tubes and part of the surface area of the sensor electrode remains dry. The ratio of wetted surface area to total surface area increases and decreases as the amount of adsorbed water increases and decreases.

Within this adsorbed water and very close to the metal surface is a layer of ionized oxygen. This layer of ions forms one layer of a parallel plate capacitor. On the surface of the metal is a layer of induced electrons. This layer of electrons is the second layer of the parallel plate capacitor. The electrical capacitance of this capacitor increases and decreases as the wetted area of the sensor electrode surface increases and decreases. But since the amount of wetted area is proportional to the amount of leakage water, the variation in capacitance becomes a measure of the variation in the amount of leakage water.

The sensor electrode must be incorporated into a complete electrochemical circuit. A wire is connected to the end of the sensor electrode outside the trunk surface. A second electrode is buried in the soil such that it is conductively connected to the roots of the tree. This location and material selection of this second electrode is such that the capacitance across the second electrode/soil interface is constant or negligible. A wire is connected to this second electrode. Then ends of the two wires connected to the two electrodes are connected to an electronic device which measures the capacitance between the two wires. The variation in capacitance moves in concert with the variation of the amount of leakage water in the sapwood.

Figure 2:
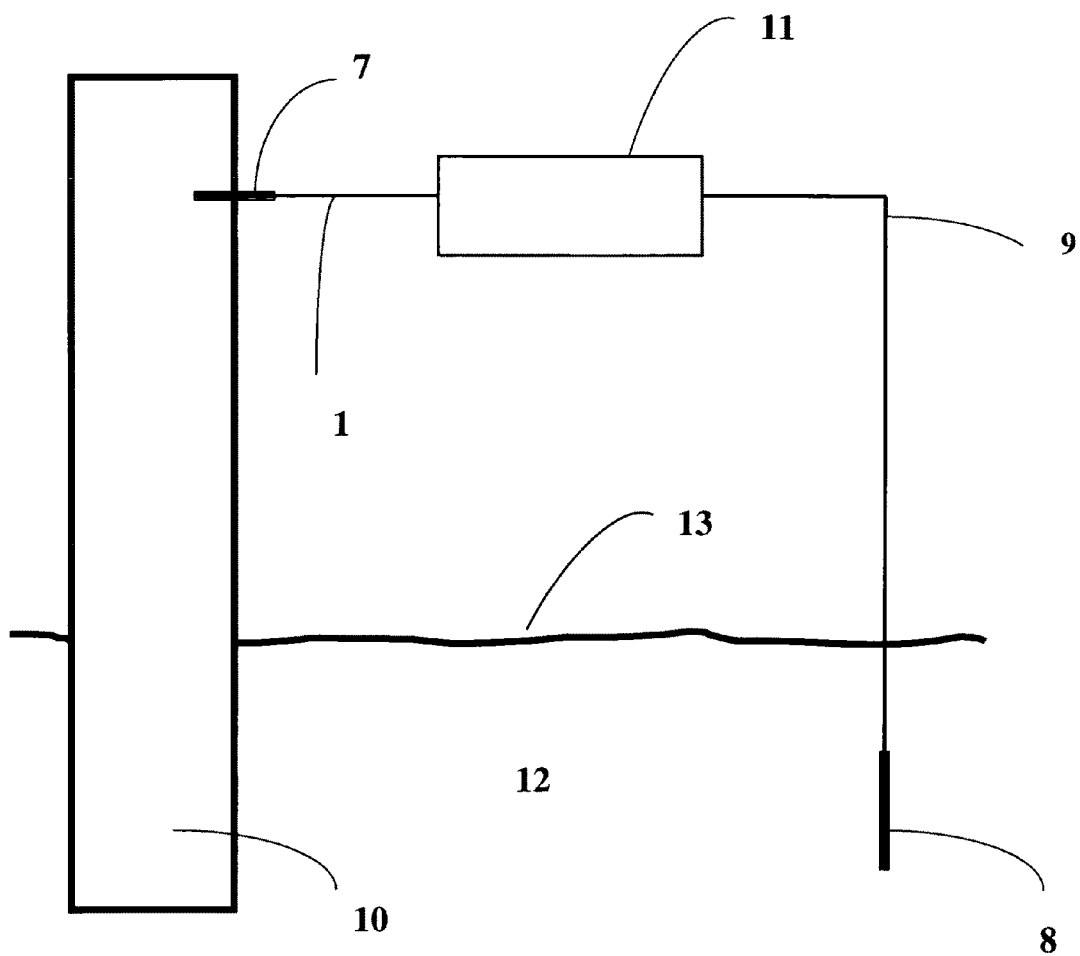

FIG. 2 illustrates the complete electrochemical circuit.

Leakage Water Content Changes Expressed on an Absolute Scale

Water content in the extraxxylary region will changes due to normal transpiration. With a pre-determination of the active surface area of the sensor electrode, the measurement expressed as a water content per unit surface area becomes absolute, that is, values obtained one year can be extrapolated to values obtained the following year. One location can be compared to another. This requires that the reported output of the measurement be expressed as a ratio of the measured capacitance to the total active surface area of the sensor electrode in the sapwood.

Measurement of the Magnitude and Timing of Recharge Water as it Passes Upward Through the Trunk The designed leaks in the xylem causes cause leakage water to move into the extraxyllary region of the sapwood. The magnitude of this leakage water can be measured by water content sensor electrodes implanted in the sapwood. The water content sensor electrode is sensitive to the amount of wetting on its surface. The wetted area increase and decreases in concert with the increase and decrease in the volume of leakage water. This change in wetted area causes a change in the capacitance of the sensor electrode surface/water interface. Measurement of changes in the capacitance are in concert with changes in the leakage water and in turn changes in the amount of water passing upward through the xylem tubes. This results in a method to measure the magnitude and timing of the recharge process.

Since the measured water content has the two components described in Eqn 1, determination of the component due to one component only requires a special procedure. The procedure is to make water content measurements before and then during the period of water application. Define the following measurements:

MWC (0)=measured water content just before water is applied; time equals zero.

MWC (t)=measured water content during water application

Then from Eqn 1 above:

$$MWC(0) = WC_D(0) \qquad (2)$$

The measurement is made before water is applied so that $WC_L$ equals zero at t equals zero.

Assume that the diurnal water content does not change significantly during the period of water application relative to the magnitude of the water content due to leakage. The data in FIG. 3 supports this assumption. Then the measured water content during the period of water application becomes $$MWC(t) = WC_D(0) + WC_L(t) \qquad (3)$$

Subtracting Eqn 2 from Eqn 3 yields $$WC_L(t) = MWC(t) - MWC(0) \qquad (4)$$

The procedure is to make a measurement of water content just before water is applied and then a sequence of measurements during water application. Subtract off the measured value before water is applied from measured value after water is applied and one is left with a net measured water content value that can be attributed to only leakage water. But leakage water is assumed to be proportional to the rehydration rate. The result is a measured variable proportional to rehydration rate.

Integration of this rate over time gives a quantitative measure of the volume of water transferred, and independently, the onset and termination of water transfer upward into the canopy. An estimate of the conversion constant required to convert from integrated rate of transfer to volume of water transferred is necessary only if one wants to determine volume.

FIG. 3 illustrates the measured water content over two successive irrigation cycles in an almond orchard in California. The rehydration pulse is superimposed on the normal diurnal cycle of water content.

Relation of the Measured Sapwood Water Content to the Decision Concerning how Much to Water Optimum water use efficiency will be attained if one can match the duration of water application to the duration of the time required for complete rehydration of the canopy. FIG. 4 illustrates the optimization procedure in graphical form. The water application period is represented as a simple rectangle indicating the turn on and turn off times for water application. The rehydration pulse is represented as a simple rectangle as well. In situation in (A) indicates the water application period is thirty-six hours in duration. This is longer than the twenty four hours required to completely rehydrate the canopy. This indicates overwatering. The water application period must be reduced in duration. In situation (B) the water application period has been reduced to twenty four hours to coincide with the rehydration pulse. Both the water application period and the rehydration pulse now have the same duration. This is optimum.

The result of this analysis is that one can set the duration of the applied water pulse to coincide with the sharp decline in the rehydration pulse. Further water application will not increase the storage of water within the canopy. Water will only be banked in the soil with the possibility that downward percolation will result in water lost and a lower water use efficiency.

FIGURES

FIG. 1 Sensor electrode implanted in the trunk
FIG. 2 Complete electrochemical circuit
FIG. 3 Example of the rehydration pulse as measured by a pulse rise in water content during water application to the soil in an almond orchard in California
FIG. 4 The three possibilities concerning the match between the duration of applied water and the duration of the rehydration pulse.

REFERENCE NUMERALS IN FIGURES

1 First Wire from sensor electrode to measuring device
2 Surface of the trunk
3 Cambium
4 Hole for implant
5 Hole for sensor
6 Implant
7 Sensor electrode
8 Second electrode
9 Second wire from second electrode to measuring device
10 Trunk
11 Measuring device
12 Soil
13 Surface of the soil
14 Water application period
15 Canopy rehydration Pulse

DESCRIPTION

FIG. 1

Placement of the sensor electrode 7 in trunk 10 is accomplished by first drilling hole 4 in trunk 10. An implant 6 is then threaded into hole 4 such that the bottom of implant 6 is past cambium 3. Sensor electrode 7 is then inserted through the hole in implant 6 and further through hole 5. This results in a known area of surface of sensor electrode 7 in homogeneous sapwood. Wire 1 attached to sensor electrode 7 connects to measuring device 11.

FIG. 2

First wire 1 is connected to sensor electrode 7 which is inplanted in trunk 10. Second wire 9 is connected to second electrode 8. The capacitance between first wire 1 and second wire 4 is measured by measuring device 11. As the sapwood water content changes the measured capacitance changes. If the capacitance of second electrode 8/soil 12 interface is constant, any change in the capacitance measured across first wire 1 and second wire 9 can be attributed to a change in the capacitance of sensor electrode 7/trunk 10 interface. The capacitance of sensor electrode 7/trunk 10 interface is proportional to the magnitude of the wetted surface area of sensor electrode 7. As the wetted surface area increases and decreases, the interfacial capacitance increases and decreases, respectively. The measured capacitance is proportional to changes in the wetted surface area of the sensor electrode 7/trunk 10 interface. Changes in the measured capacitance then indicates changes in the water content of the sapwood of trunk 10.

Part of the surface area of sensor electrode 7 is covered with water and part of the surface is covered with air. Changes in the measured capacitance can be larger or smaller depending on the magnitude of the total surface area of sensor electrode 7 in trunk 10. The measured capacitance is divided by this total surface area to form a ratio of measured capacitance to total surface area. The changes in this ratio become a measure of changes in trunk 10 water content. The reported output has the units of farads/meter squared.

CONCLUSIONS

The basic conclusion is that the presence of designed leaks in the xylem tubes permits the water content measurement to function as a water flow measurement during the time interval of water application. The procedure outlined above results in a definitive quantification of the duration of the flow. The conversion from a flow rate to a flow volume is possible only with estimates of the relation between leakage and volume flow. However, the rapid decline in rate once complete canopy storage was been reached is clearly definable. This permits one to make the decision on how much to water without the necessity of an exact determination of the volume of water transferred.

RAMIFICATIONS

Relation of the Optimum Duration of the Rehydration Pulse to the Transpiration Rate If the duration of the rehydration pulse is set to coincide with the duration of the applied water, then the time integral of the measured water content become proportional the total transpiration between water applications. This permits a quantification of the total transpiration over the multi-day period between water applications. The widely used Evapotransiration Index (ET) can be related to this total transpiration value if one can assume that the dominant water loss comes from transpiration. This assumption is quite probable in moderately aged orchard.

SCOPE OF THE INVENTION

While there have been illustrated and described various embodiments of the present invention, it will be apparent to those skilled in the art that modification thereof will occur to those skilled in the art. It is intended in the appended claims to cover all such changes and modifications that fall within the true scope and spirit of the present invention.

I claim:

1. A method of measuring canopy rehydration of a plant comprising the steps of:
    measuring the surface area of a sensor electrode,
    placing said sensor electrode in the sapwood of said plant,
    placing a second electrode in the soil of said plant,
    measuring the electrical capacitance between a first wire connected to said sensor electrode and a second wire connected to said second electrode,
    forming a ratio of said electrical capacitance to said surface area of said sensor electrode,
    determining the value of said electrical capacitance during the period just prior to water application,
    determining the value of said electrical capacitance during said period of said water application,
    determining the difference between said value of said capacitance measured during said period just prior to said water application and said value of said capacitance during said period of said water application,
    integrating said difference over said period of said water application.

* * * * *